United States Patent [19]

Gersten et al.

[11] Patent Number: 4,772,115
[45] Date of Patent: Sep. 20, 1988

[54] ILLUMINATED RING KERATOMETER DEVICE

[75] Inventors: Martin Gersten, Brooklyn; Richard J. Mammone, Woodmere; Joseph Zelvin, Larchmont, all of N.Y.

[73] Assignee: Computed Anatomy Incorporated, New York, N.Y.

[21] Appl. No.: 902,610

[22] Filed: Sep. 2, 1986

[51] Int. Cl.[4] .......................... A61B 3/10; A61B 3/14; G01B 9/00

[52] U.S. Cl. .................................. 351/212; 351/206; 362/32; 356/124

[58] Field of Search ............... 351/212, 247, 206, 211, 351/212, 237; 362/32; 356/124

[56] References Cited

U.S. PATENT DOCUMENTS 3,598,478 8/1971 Townsley ............................ 351/212

OTHER PUBLICATIONS

"New Photo Keratoscope Utilizing a Hemispherical Object Surface", by Henry A. Knoll et al, Journal of the Optical Society of America, vol. 47, #3, p. 221.

Primary Examiner—Rodney B. Bovernick
Assistant Examiner—Jay P. Ryan
Attorney, Agent, or Firm—Howard R. Popper

[57] ABSTRACT

A device for causing concentric circles of illuminated light to be reflected from the human cornea. The device includes a cylindrical surface which is open at both ends. At one end the eye looks into the cylinder of the device and at the other end a camera or observer can view the illuminated rings on the cornea. The cylinder is advantageously made of transparent plastic or glass having an opaque coating. A lamp box is affixed to an uncoated portion of the device. The coating of the cylindrical surface through is interrupted to define clear rings on the cylindrical surface which light from the lamp box is conducted to be reflected from the cornea.

5 Claims, 4 Drawing Sheets

ILLUMINATED RING KERATOMETER DEVICE

FIELD OF THE INVENTION

This invention relates to apparatus for observing the cornea of the human eye and more particularly to an apparatus for causing concentric bright rings to be reflected from the cornea to facilitate the performance of corneal transplant surgery, corneal keratotomy or the fitting of contact lenses.

DESCRIPTION OF THE PRIOR ART

Heretofore a number of optical devices have been available for projecting one or more illuminated rings upon the cornea of a patient's eye. These illuminated rings are useful in determining the radius of the cornea as a step in correctly fitting contact lenses. Another use is found in corneal transplant surgery where the distortion of an illuminated ring reflected from the cornea enables the eye surgeon to determine whether the suturing of the transplant in place has resulted in any undesired deformity, known as corneal astigmatism.

Kilmer, et al, U.S. Pat. No. 3,797,921, issued Mar. 19, 1974, shows one type of light ring projection apparatus. Lange, et al., U.S. Pat. No. 4,172,639, issued Oct. 30, 1979, shows another type of device which is suggested for use with an operating microscope.

While the Lange patent device is quite compact, it is capable of causing only a single ring to be reflected from the corneal surface. The same is true of the handheld keratometer of the Holcomb U.S. Pat. No. 4,426,141, issued Jan. 17, 1984, and of the Kariaschoff U.S. Pat. No. 4,491,398, issued Jan 1, 1985. The Kilmer patent device, which is capable of projecting a plurality of rings on the cornea is, for reasons to be hereinafter explained, required to be much larger in diameter than devices of the Lange or Holcomb patent types. It would be extremely advantageous to provide a device capable of causing any desired number of illuminated rings to appear on the cornea of the patient's eye but which, nevertheless, was more compact than that of the Kilmer patent type.

We have discovered that the size of the prior art keratometers may have been dictated by the need to overcome the difficulty encountered when attempting to project illuminated rings upon more than the most central portion of the cornea. Because the cornea is curved, light that is projected on to the cornea in beams that are parallel to the corneal axis will be reflected at an angle to the corneal surface and at increasingly divergent angles to the corneal axis proportional to their distance from that axis. Parallelly projected beams of light that strike the corneal surface further from corneal apex (i.e., those striking closer to the corneal limbus) will be reflected at a larger angle to the corneal axis than light striking closer to the corneal apex. Since the observer would normally look at the patient's eye more or less directly in line with the corneal axis, parallelly projected light striking near the limbus is not returned to the observer. Accordingly, it has heretofore been necessary to compensate for these greater angles of reflection by projecting the illuminated rings from a light source which is several times the diameter of the cornea. Further, it has not heretofore been practical to project more than about 9 or 10 rings on the patient's cornea and these rings have been confined to the region that is less than about half of the distance to the corneal limbus.

SUMMARY OF THE INVENTION

In accordance with the principles of the present invention, an apparatus for causing any desired number of illuminated rings to appear on the cornea of a patient is achieved which need be no larger in diameter than that of the Lange patent device, for example, and which need be only slightly larger in diameter than that of the patient's eye. Moreover, the rings may be reflected from almost the entire surface of the patient's cornea, i.e., from the corneal apex to almost the corneal limbus.

In accordance with one illustrative embodiment of our invention, an illuminated ring keratometer device comprises a truncated conical body of transparent plastic having a cylindrical, largely opaquely coated passageway therethrough. The passageway opens to a port dimensioned to be positioned close to the patient's eye. A number of equal diameter circular rings are described through the opaque coating to reveal the bare plastic, the rings being more closely grouped toward the eye-port end of the passageway. The base of the conical body at the posterior end of the passageway remote from the eye-port is mounted in a housing in which a lamp is exposed to the bare plastic so as to enable light to be conducted therethrough so as to provide backlighting to the series of described rings.

The illuminated rings closest to the open, eye-port end of the passageway illuminate that portion of the patient's cornea that is closest to the limbus while the illuminated rings further down the passageway illuminate the more central portions of the cornea closer to the corneal apex. Positioned part way down the passageway and at an angle to the central axis of the passageway is a thin sheet of glass or plastic which is basically transparent but which exhibits a small degree of reflectivity to act as a pellicle. A small advantageously colored, beam of light is aimed at the pellicle surface so as to be reflected toward the open eye-port end of the passageway and thereby serve as a fixation target or center of attention for the patient's eye to focus upon. The colored dot of light is also reflected upon the surface of the cornea as an apical spot. The observer may then employ a camera to photograph the patient's eye with the illuminated rings and apical spot thereon to make measurements of the ring-to-apical spot distances.

BRIEF DESCRIPTION OF THE DRAWINGS

The foregoing and other objects and features of the present invention may become more apparent from the ensuing description and drawing in which.

GENERAL DESCRIPTION (FIGS. 1 AND 5)

Figure 1:
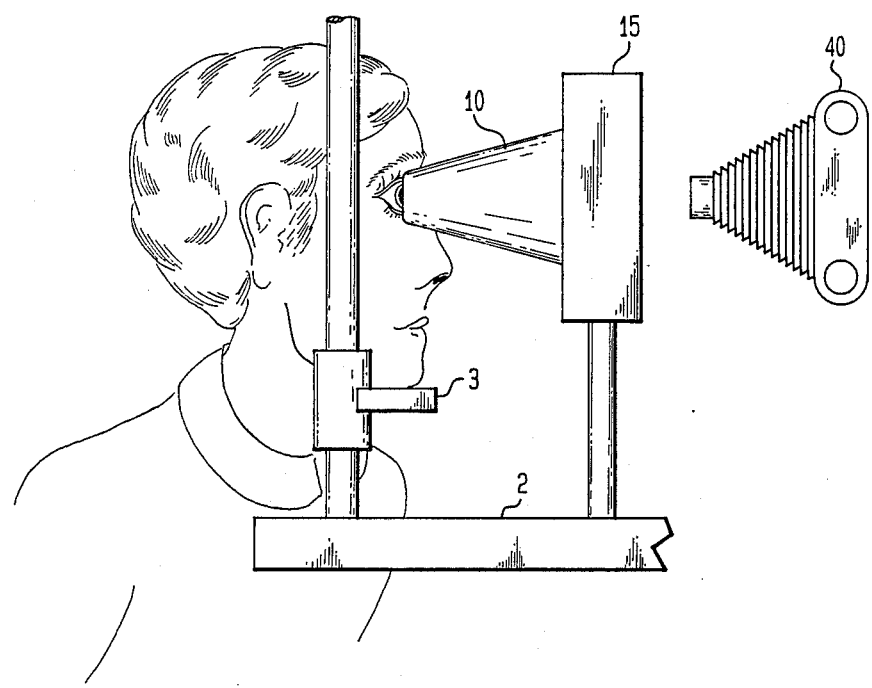
FIG. 1 shows a side view of one embodiment of the illuminated ring projection device of our invention mounted in a stand such as that commonly used for a slit lamp apparatus.

Referring now to FIG. 1, there is shown the apparatus of our invention mounted in a stand such as that commonly used to support a slit lamp apparatus. The patient positions his chin on the chin rest 3 of the stand and looks into the eye-port end of cone 10. The base of cone 10 remote from the eye port end is fastened to light box 15. A recording camera 40 is positioned in line with the corneal axis at the end of light box 15 opposite the base of cone 10.

Figure 5:
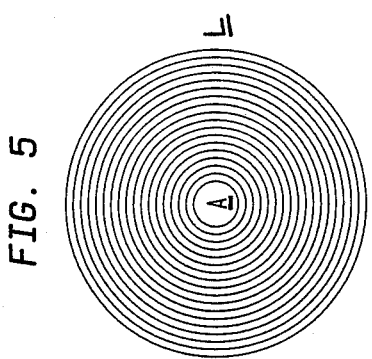
FIG. 5 shows the series of concentric illuminated rings and apical spot as they would be reflected from the cornea of a patient's eye.

FIG. 5 shows in enlarged detail the series of concentric, equally spaced circles, approximately 18 in number, as drawn from a photograph of patient's cornea obtained by recording camera 40. As can be seen, the circles cover almost the entire surface of the cornea from the corneal apex A to the limbus L.

DETAILED DESCRIPTION

Figure 2:
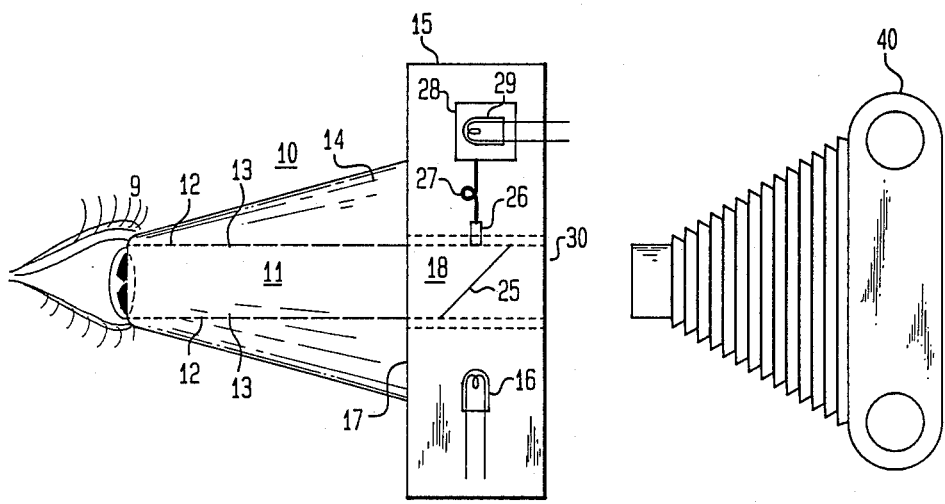
FIG. 2 shows an enlarged cross-sectional view of one embodiment of FIG. 1.

Referring to FIG. 2, one embodiment of the cone 10 and light box 15 is shown in an enlarged view. Cone 10 is hollow, containing a basically cylindrical passaeway 11 whose axis is intended to coincide with the corneal axis when the patient looks into the open eye-port end 9. Cone 10 is advantageously fabricated of clear plastic material such plexiglass. Outer surface 14 of cone 10 advantageously tapers from eye-port end 9 at its left-hand extremity toward base 17 which may be cemented or otherwise fastened to light box 15.

Figure 3:
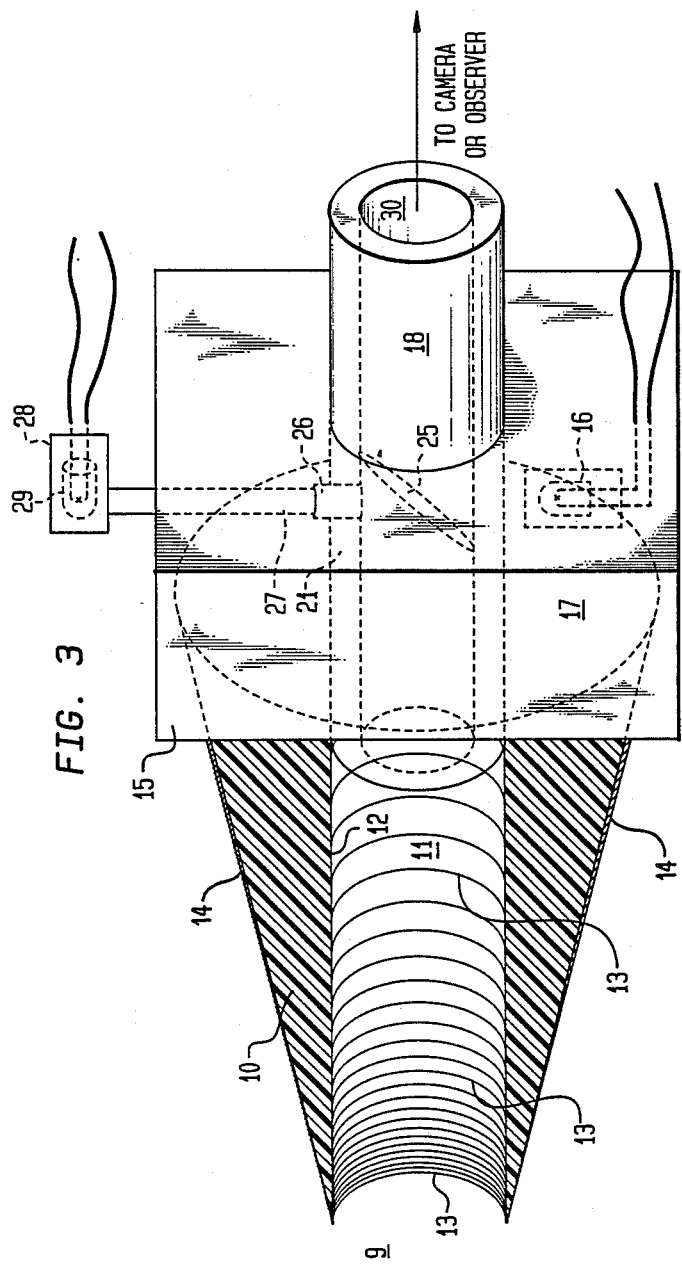
FIG. 3 shows further details of another embodiment of FIG. 1, in isometric section.

Extending from light box 15 (best seen in the embodiment of FIG. 3) is a cylindrical central tube 18 which is intended to be coaxial to cylindrical passageway 11 of cone 10. The left-hand end of tube 18 opens to cylindrical passageway 11 while the right-hand end of tube 18 opens to observer port 30 through which the eye surgeon, optometrist or recording camera 40 may view the patient's cornea. Tube 18 may advantageously extend a short distance into passageway 11 to facilitate attachment of box 15 to cone 10.

Within light box 15 one or more lamps 16 are provided in such fashion as to uniformly illuminate the base portion 17 of translucent cone 10. Light box 15 has been illustratively fabricated of plastic but is advantageously fabricated of metal or other opaque material, having a number of illuminating holes (not shown) provided in its left-hand wall adjacent to base 17 of cone 10 so that light from lamp 16 may enter the base portion 17 of translucent cone 10 and be conducted therethrough to back-light rings 13. Light is prevented from escaping through outer surfaces 14 of cone 10 and of box 15 by painting surfaces 14 with an opaque coating of any desired color.

The interior surface of passageway 11 is also provided with an opaque coating 12 which is preferably black. Interior opaque coating 12, however, is selectively machined away to define an array of circular arcs of rings 13. The light from lamp 16 passes through the translucent left-hand face of box 15, enters the base region 17 of cone 10 and is conducted through cone 10 causing each of rings 13 to be illuminated.

In order to give the patient something to focus on, passageway 11 is provided with a pellicle 25 positioned centrally in the passageway and at an angle to its axis. Optical fiber 27 and lens 26 aim a tiny spot of colored light, such as a red dot, toward the center of the pellicle by coupling light from red lamp 29 which is positioned in cavity 28 mounted within box 15. The red dot is reflected by pellicle 25 toward the patient's eye so as to appear at the apex A of the patient's cornea (see FIG. 5).

Figure 6:
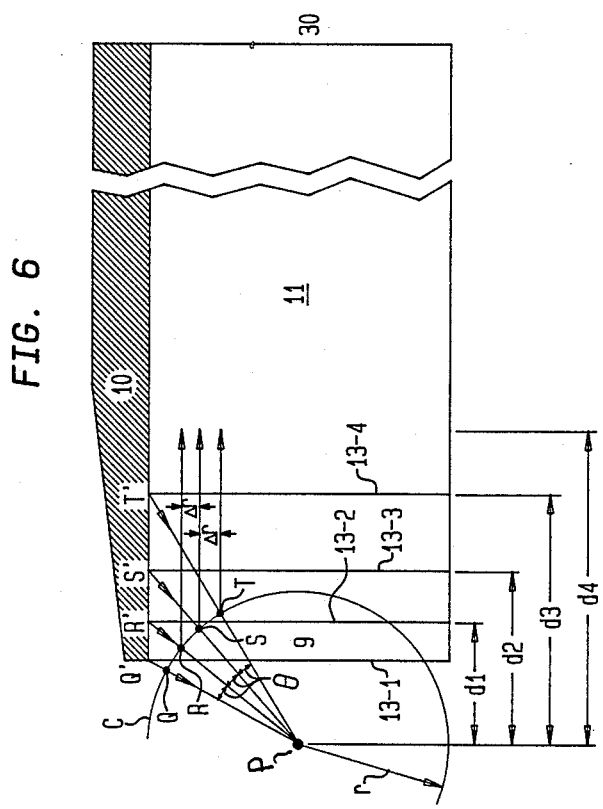
FIG. 6 shows in schematic form the manner of laying out the rings for the apparatus of our invention.

The manner in which the illuminated rings 13 are laid out in passageway 11 and in which the illuminated rings cause circles to be projected toward the patient's cornea is most clearly shown in FIG. 6. Assuming that a surrogate for the patient's eye can be described as a sphere C having a radius r of 7 millimeters, the center of the sphere may be represented (in two dimensions) as being positioned at point P located a distance d1 approximately 3 millimeters to the left of eye-port end 9 of passageway 11. A schematic layout of rings 13 may then be constructed by projecting successive radii r from point P separated from each other by substantially equal angles $\theta$. The illustrative radii first intersect the surface of sphere C at points Q, R, S and T and then strike internal surface of passageway 11 at points $Q^1$, $R^1$, $S^1$, and $T^1$, respectively, to define the locations at which rings 13-1, 13-2, 13-3, and 13-4 are to be cut. An internal boring tool (not shown) may then be programmed to cut rings 13-1, 13-2, 13-3 and 13-4 at axial distances d1, d2, d3, and d4, respectively, down passageway 11 from point P at eye-port end 9.

Light from back-lit rings 13-1 through 13-4 is reflected upon the surface of sphere C. Note that the incremental radial distances $\Delta r$ between the rings as reflected from the surface of sphere C appear to the observer at point 30 to be smaller than the corresponding arc lengths R-S, S-T, etc. on the surface of the sphere. FIG. 5 shows how the ring so reflected from the surface of sphere C would appear to such an observer or camera 40.

Figure 4:
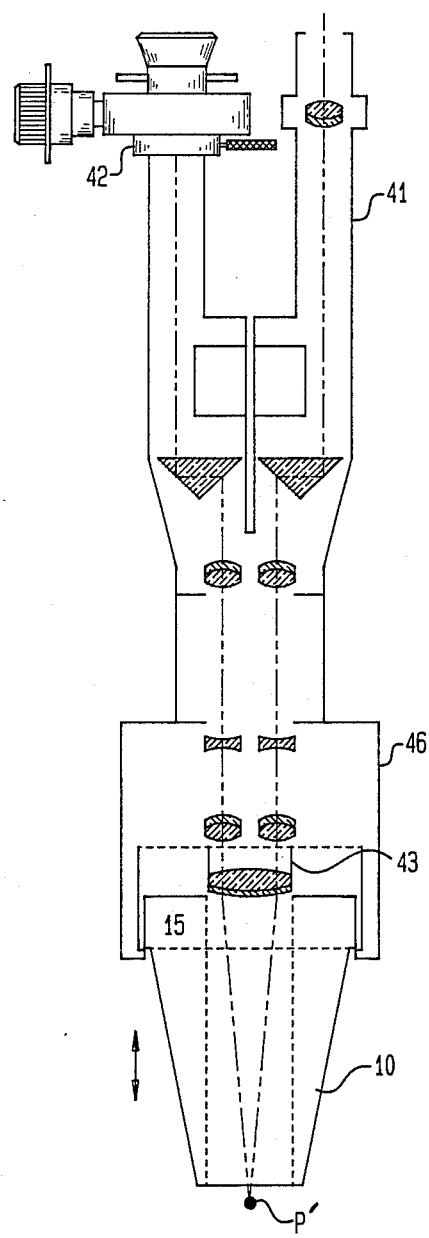
FIG. 4 shows an alternative embodiment mounted on a binocular operating microscope.

FIG. 4 shows a binocular operating microscope 41 of conventional design which has been modified in accordance with our invention. Advantageously one eyepiece may be fitted with the micrometer reticule 42 of the type shown in Lange et al U.S. Pat. No. 4,172,639 previously mentioned. Instead, however, of employing the Lange patient's plexiglass tubing at the objective lens 43 to project only a single ring upon the patient's cornea, the operating microscope embodiment of our invention is fitted with a shroud 46 in the region of objective lens 43. Shroud 46 slidably accommodates our above-described cone 10 and light box 15 assembly. The cone and light box assembly 10, 15 is shown in its downmost position within shround 46 in which position it is employed to project the plurality of rings on the patient's cornea. The cone and light box assembly may then be slid to its uppermost position within shroud 46 so as to provide additional clearance at the surface of $p^1$ of the cornea in the surgical field to facilitate performance of surgical procedures. Note that upward and downward motion of assembly 10, 15 may be accomplished without changing the focus of the microscope since the distance between objective lens 43 and point $P^1$ of the surgical field remains fixed regardless of the motion of assembly 10, 15. Pushbutton control of such upward and downward motion may be provided by equipping shroud 46 with a solenoid (not shown).

What has been described is illustrative of the principles of our invention as portrayed by the illustrative embodiments. Further and other modifications, such as modifying the spacing of rings 13 to accommodate the departures of the human cornea from the contours of the idealized sphere which has been described herein may be apparent to those skilled in the art without, however, departing from the spirit and scope of our invention.

What is claimed is:

1. Apparatus for projecting illuminated arcs over a portion of curved surface comprising
   a body of transparent material including a substantially cylindrical, opaquely coated passageway therethrough having at one end an opening proportioned to accommodate a portion of said curved surface, said cylindrical passageway having an internal diameter commensurate with the diameter of said portion of said curved surface accommodated at said opening, said opaque coating being relieved to bare said material along a series of arcs positioned on the wall of said passageway, said arcs being progressively spaced more closely to each other toward said opening at said one end, and
   means for illuminating said transparent body to back-light said series of arcs.

2. The apparatus of claim 1 wherein said passageway includes a pellicle positioned at an angle to the axis of said passageway, and means for projecting a spot of light toward said pellicle so as to be reflected toward said opening at said one end.

3. Apparatus for causing a series of illuminated rings to be reflected from the cornea of a patient's eye, comprising
   a hollow body of transparent plastic having a conical, opaquely coated exterior and a hollow interior, said exterior terminating in a coating-free frustrum portion and said interior being defined by a first and a second concentric cylinder (11,18) each having an opaquely-coated internal surface having a diameter commensurate with that of the eye, said first cylinder having an internal diameter dimensioned to admit a portion of the eye's cornea at one end thereof, said second cylinder being positioned within and toward the other end of said first cylinder, said opaque coating being selectively relieved to define a plurality of bare, transparent circular arcs on at least one said cylinder, and
   means including a light box adjoining said coating free frustum portion for back-lighting said circular arcs.

4. Apparatus according to claim 3 wherein a portion of said internal diameter of said cylinder remote from said one end is proportioned to accommodate the objective lens of an operating microscope.

5. Apparatus according to claim 4 further comprising a shroud affixable to said operating microscope and adapted to retain said cylinder in slidable relationship along the axis of said objective lens.

* * * * *